United States Patent [19]

Feller et al.

[11] Patent Number: 4,657,851

[45] Date of Patent: Apr. 14, 1987

[54] BREAST CANCER DIAGNOSTIC BLOOD TEST

[75] Inventors: William F. Feller, Bethesda; Judith A. Kantor, Rockville, both of Md.

[73] Assignee: Georgetown University, Washington, D.C.

[21] Appl. No.: 567,671

[22] Filed: Jan. 3, 1984

[51] Int. Cl.$^4$ .................. G01N 33/53; G01N 1/00; G01N 33/48; G01N 33/566

[52] U.S. Cl. .................. 435/7; 436/501; 436/63; 436/64; 436/174; 436/176; 436/548; 436/825

[58] Field of Search .................. 435/7; 436/825, 500, 436/548, 813, 63, 64, 174, 175, 177, 178, 501

[56] References Cited

U.S. PATENT DOCUMENTS

| | | | |
|---|---|---|---|
| 3,502,546 | 3/1970 | Thompson et al. | 435/42 |
| 4,056,608 | 11/1977 | Ullman et al. | 424/1 |
| 4,299,812 | 11/1981 | Coombes | 421/1 |
| 4,322,495 | 3/1982 | Kato | 435/7 |
| 4,362,531 | 12/1982 | deSteenwinket et al. | 23/230 B |
| 4,379,135 | 4/1983 | Sasaki | 436/536 |
| 4,493,898 | 1/1985 | Sallay | 436/64 |

OTHER PUBLICATIONS

Ceriani et al., Proc. Nat'l. Acad. Sci. USA, vol. 79, pp. 5120–5124, 1982.

*Primary Examiner*—Christine M. Nucker
*Assistant Examiner*—Patricia L. DeSantis
*Attorney, Agent, or Firm*—Oblon, Fisher, Spivak, McClelland & Maier

[57] ABSTRACT

A method for detecting an antigen in a plasma or serum sample, which comprises conditioning the sample, wherein conditioning comprises either diluting the sample by a factor of at least 100 or dissociating the antigen in the sample from binding proteins with acid, base, or a chaotropic agent; drying the conditioned sampled; and detecting the antigen in the dried sample using an immunological assay is disclosed. The method is particularly useful for the detection of antigens associated with breast cancer.

8 Claims, No Drawings

BREAST CANCER DIAGNOSTIC BLOOD TEST

BACKGROUND OF THE INVENTION

1. Field of the Invention:

This invention is related to diagnostic assays for the detection of antigens in blood and particularly to diagnostic assays relating to the detection of antigens associated with breast cancer.

2. Description of the Prior Art:

Carcinoma of the breast is the most frequent form of cancer in women in North America and Europe. The traditional diagnostic technique of palpation is often insuffient for the detection of early lesions. Often, by the time that a malignant mass becomes distinguishable from a benign nodule of breast tissue, the cancer has metastasized. The principal alternative merhod of detecting breast malignancies in recent years is the mammogram, a low-voltage X-ray procedure. However, because of the oncogenic potential of this X-ray procedure, the method is of limited usefulness in premenopausal women. Current guidelines of the National Cancer Institute recommend that routine mammography be restricted to women over 50 and to high-risk patients under 50. There accordingly remains a need for a non-invasive method of detecting early malignancies of the breast.

One method of detecting cancer which has received considerable attention in recent years is the use of immunological techniques for detecting antigens associated with cancers. The best known such antigen is carcinoembryonic antigen (CEA). When first discovered, CEA was thought to be specific to cancers of the digestive system. However, CEA has since been detected in normal adults as well as in patients with benign liver disease, such as alcoholic hepatitis or biliary obstruction. Because of the overall lack of specificity and sensitivity, there being no threshold difference in CEA levels that serves to separate benign from malignant conditions, CEA cannot be used as a general diagnostic test. It is principally used in the monitoring of response to treatment.

Similar antigens are now known to exisr in breast cancer. Breast tissue markers such as casein [Franchimont et al, *Cancer*, 39, 2806–2812 (1977)] and α-lactalbumin [Kleinberg et al, *Science*, 190, 276–278 (1975)] and proported cancer markers such as glycosyl transferases [Ip et al, *Cancer Res.*, 38, 723–728 (1978); Dao et al, *J. Natl. Cancer Inst.*, 65, 529–534 (1980)], glycolipids [Kloppel et al, *Proc. Natl. Acad. Sci. USA*, 74, 3011–3013 (1977)], and phospholipids [Skipsky et al, *Proc. Soc. Exp. Biol. Med.*, 136, 1261–1264 (1971)] have all been used in various diagnostic techniques for breast cancer without gaining widespread acceptance as a breast cancer marker. More recently, circulating human mammary epithelial antigens have been proposed as specific markers for breast cancer [Ceriani et al, *Proc. Natl. Acad. Sci. USA*, 79, 5420–5424 (1982)].

However, one recurring problem in the immunological detection of any antigen present in blood (not just in tests for antigens associated with cancer) is the occurrence of false positive and false negative reactions. For example, in the area of cancer diagnosis, false positives can result in unnecessary diagnostic surgery or mammography of a patient who does not have cancer, while false negatives result in cancer that goes undetected. Accordingly, a method for improving the discrimination of immunological assays and eliminating false positives and false negatives to the maximum extent possible is needed both in the general area of antigen detection and particularly in the detection of life-threatening malignancies.

SUMMARY OF THE INVENTION

Accordingly, it is an object of the present invention to provide a diagnostic technique for use with immunological assays for antigens present in blood which increases the reliability of the assay technique.

It is a further object of this invention to provide a method specific for the diagnosis of breast cancer utilizing this method of improved specificity.

These and other objects of the invention as will hereinafter become more readily apparent have been accomplished by providing a method for antigen detection in a blood sample, which comprises conditioning said sample, wherein conditioning comprises either diluting said sample by a factor of at least 100 or dissociating said antigen in said sample from binding proteins with acid, base, or a chaotropic agent to give a conditioned sample; drying said conditioned sample onto the surface of a test container to give a dried sample; and detecting said antigen in said dried sample using an immunological assay.

DESCRIPTION OF THE PREFERRED EMBODIMENTS

The present invention arose as the result of studies in the laboratories of the inventors which indicated that the specificity of a diagnostic test for an antigen present in blood could be improved by using a process which dissociates antigens from antibodies already present in the blood sample. This dissociation process of the invention is usually associated with a concurrent dilution of the sample, and the entire process of diluting and dissociating is termed "conditioning" for the purposes of this application. After the sample is conditioned, it is dried onto the surface of a test container, after which the antigen can be identified by standard methods of immunological diagnosis. Surprisingly, the combination of conditioning and drying the sample prior to immunological analysis greatly enhances the reliability of the immunological test procedure. This discovery has now been developed into the complered invention which is set forth in this application for patent.

The present assay technique is designed for utilization with a plasma or serum blood sample. Plasma samples are preferred since the clotting process often removes antigens from the aqueous phase of blood. Although the principal objective of this invention is the detection of antigens in human blood, blood from animals, particularly mammals, can also be tested in the same way.

When the conditioning process of this invention involves dilution, dilution by at least a factor of 10 and more preferably by a factor of at least 100 is preferred. Particularly preferred are dilutions in the range of 100- to 1000-fold. The conditioning process may optionally comprise the use of a chaotropic agent or a disruptive condition (whether or not a dilution is used) which results in the dissociation of immunological complexes in the blood sample. A chaotropic agent or disruptive condition is required if dilutions of less than 100-fold are used. A chaotropic agent or disruptive condition is a chemical agent or a condition that disrupts the forces involved in the bonding of antigen/antibody complexes. They include vander Waals forces, coulombic forces, ion attractive forces, and hydrogen bond forces. Chaotropic agents interact with and dissociate immune complexes by ionic substitution. Typical chaotropic agents include solutions of KI, KCN, and KSCN and will be described in more detail at a later time. Typical disruptive conditions are the use of acid or base which result in pH values outside the normal range of physiological pHs. In this application, adjustment of pH by means of an appropriate buffer is referred to as a "condition" rather than as the use of an "agent" since the condition is described in terms of the pH value obtained and does not depend on the particular agent used to obtain the stated pH. Chemical compounds whose structure and individual properties are important in obtaining the resulting dissociation of immunological complexes are referred to as "agents", more specifically as "chaotropic agents", rather than as conditions.

When the sample is diluted by a factor of 100 or more, chaotropic agents or disruptive conditions are not essential but may be used if desired. However, when dilutions are not carried out, it is essential that a chaotropic agent or disruptive condition suitable for dissociating immunological complexes be present. A combination of dilution in the range of 10-to 1000-fold and use of a chaotropic agent or disruptive condition is especially preferred.

The preferred disruptive condition for use with this aspect of the invention is low pH. By low pH is meant from 2 to 5, preferably from 2 to 4, and more preferably from 2 to 3. Suitable buffers for establishing the necessary pH ranges include citrate, citric acid, or a mixture of dilute hydrochloric acid and glycine. Buffers are made up according to standard methods known to those skilled in the art thereof and can be prepared for any desired value in the stated ranges. Suitable techniques are well known and are described in, for example, *Handbook of Chemistry and Physics*, 48th Ed., Weast and Selby, eds., The Chemical Rubber Co., Cleveland, Ohio, 1967, pages D-78 and D-79, which are herein incorporated by reference. Buffers having a concentration of 20 to 100 mM are preferred. Examples of chaotropic agents suitable for this conditioning step include $SCN^-$, $CN^-$, $I^-$, $Br^-$, and $Cl^-$, which decrease in disruptive activity in the order given. Typical concentrations of such agents are from 0.5 to 2.5M. Particularly preferred agents and concentrations include 0.5M KI, 2.5M NaSCN, and 2.5M PVP-Iodide (a commercially available polyvinylpyrrolidine composition containing 10.3% iodine available from Sigma Chemical Co.). When high pH is used as a disruptive condition, values of 9 to 12 are preferred with values of 9 to 11 and 9 to 10 being more preferred and most preferred, respectively.

It will be apparent to those skilled in the immunological art that the exact chaotropic agent or condition and the paramerers thereof which work best for any particular antigen will vary with the antigen. However, the best conditions for a particular antigen can easily be determined if the following procedure is carried out. Precipitate the immune complexes in a sample with any suitable agent, such as polyethylene glycol. Divide the precipitated complexes into aliquots and treat the individual aliquots with the chaotropic agent or condition which is being tested, varying the concentration, temperature, etc., as is appropriate for determining optimum conditions. Determine the degree of dissociation of the complex by any suitable technique, such as electrophoresis on an agarose gel. Then choose the conditions and agents which result in maximum dissociation of the immune complex without undue loss of the ability of the antigen to complex with the antibody used in the analytical step (described in more detail in a later section).

After the sample has been conditioned, it is dried onto the walls of the container in which subsequent testing will take place. The material from which the container is made is not important for many antigens, although glass and plastic are preferred support materials in general. Because of the ease with which they may be manipulated, plastic microtiter plates are particularly preferred containers. For some antigens and analytical processes, however, the choice of support material will be important. For example, a particularly preferred support material for use in the determination of human epithelial differentiation antigens in blood (as an indication of breast cancer) is polystyrene, especially when subjected to coronal discharge treatment prior to use in the assay. Microtiter plates are commercially available in this form, for example, from Costar, 205 Broadway, Cambridge, Mass. 02139 (who identifies such plates as Tissue Culture Clusters).

After the sample is added to the container, the aqueous phase is gently evaporated. Some heat may be applied but it is preferred that the temperature of the samples not be raised to more than 55° C., preferably not more than 42° C. One preferred method of drying the samples which is parricularly useful when microtiter plates are used as the sample containers is overnight drying in an oven at 37° C. Other suitable drying techniques include use of a blow dryer ("hair dryer") on a low setting. Dried samples can be processed through the remaining steps of the analytical procedure immediately after drying if desired. However, satisfactory results will also be obtained if a delay occurs between drying and the next processing step. Delays of up to 36 hours are generally possible, but delays of less than 24 hours are preferred. Overnight drying and the resulting delays at dryness (e.g., 10–15 hours dryness) are most preferred at 37° C.

If a chaotropic agent or disruptive condition has been used which will interfer with the immunological binding that rakes place during the later detection step, it is preferred to wash the dried sample with a suitable wash solution to remove dried salts, acids, bases, or other inorganic or low molecular weight organic substances. Typically this is done using a buffered solution and most typically using the same buffered solution that is used to dilute the antibody in the detection step. A typical wasn solution is phosphate buffered saline (PBS); 10 mM phosphate, 0.9% NaCl, pH 7.4. The dried sample is washed several times (typically 3–4 times) with a volume of wash solution appropriately sized for the container and sample size being used. If desired the discarded wash sample can be tested and washing can be continued until the chaotropic agent or condition has been removed completely and can no longer be detected in the discarded wash solution, although this is generally not necessary.

After the aqueous phase has evaporated and the serum or plasma sample has been dried onto the walls of the container (and optionally washed), the antigen present in a sample is detected using standard immunological techniques. Although such techniques are easily within the skill of those knowledgeable in the immunological art, a suitable general technique will be summarized here for convenience. For further information, if necessary, see Chard, *An Introduction to Radioimmunoassay and Related Techniques,* North-Holland Publishing Company, 1978, which is herein incorporated by reference.

Typically, a buffered solution containing an antibody specific for the antigen being detected would be added to the container having the sample dried on its walls. Since immunological binding reactions typically work best at or near physiological pH, it is preferred to maintain a pH in the range of from 5 to 9, more preferably from 7 to 8, by use of a suitable buffer. Suitable buffers include PBS and Tris. Buffers and other materials in the test solution should be present in amounts such that the ionic strength of the solution is maintained ar or near normal physiological levels.

The amount of antibody present in the diagnostic solution can be varied in accordance with the amount of antigen expected to be present as is well known to tnose skilled in the art. Typically, the amount used is determined by simple experimentation for each new batch of antibody using serial dilutions to determine the optimum amount, as is well known to those skilled in the art.

Numerous antibodies are commercially available for diagnostic testing, and the production of such antibodies need not be set forth here in detail. Either polyclonal antibodies or monoclonal antibodies may be used, depending on the antigen being detected. It is particularly preferred to use monoclonal antibodies, especially for the antigens associated with breast cancer, in order to maximize specificity of the reaction and reduce the number of false positives. Particularly preferred monoclonal antibodies for use in detecting breast cancer are those identified as 115D8 (Mam-6a) and 67D11 (Mam-3a) by Antoni van Leeuwenhoekhuis, Het Nederlands Kanker Instituut, Amsterdam, Netherlands. These are monoclonal antibodies against human mammary epithelial differentiation antigens produced by mouse/mouse hybridomas and are readily available from the indicated source. See, for example, Rasmussen et al, *Breast Cancer Research and Treatment,* 2, 401–405 (1982); Hilkens et al, *Protides of the Biological Fluids,* 29, 813–816 (1982); Hilkens et al, "Monoclonal Antibodies Against Human Milkfat Globule Membranes Useful in Carcinoma Research," *Proceedings of the Biological Fluids,* 31 (1983) and Hageman et al, "Sweat Glands and Salivary Glands as Model System for the Characterization of Monoclonal Antibodies Against Differentiation Antigens of the Human Mammary Gland," *Proceedings of the Biological Fluids,* 31 (1983), all of which are herein incorporated by reference, for a discussion of these antibodies.

Antigen is detected by utilizing a signalling reagent attached to the antibody which, after suitable washing steps, remains in the test conrainer only if it has become bound to antigen coated on the test container walls. Many signalling techniques are known to those skilled in the art and need not be innumerated here in detail. However, examples of suitable techniques include radioactive labeling of the antibody, attachment of an enzyme ro the antibody (ELISA assays), and fluorescent labeling of the antibody.

As was discussed previously, the present invention can be applied to the detection of any antigen in blood. However, it is particularly suited for use in the detection of human mammary gland epithelial differentiation antigens in plasma, and the preferred conditions set forth in this application are particularly adapted to that purpose. By adhering to the critical condirions set forth in this application when used for this purpose, it is possible to achieve markedly superior reliability in a test for these antigens, which are associated with the presence of breast cancer.

The invention now being generally described, the same will be better understood by reference to certain specific examples which are included herein for purposes of illustration only and are not intended to be limiting of the invention or any embodiment thereof, unless specified.

EXAMPLES

Studies on Plasma Samples of Breast Cancer Patients Using an ELISA Technique Studies were carried out using an ELISA type assay and two Dutch monoclonal antibodies. These studies demonstrated the presence of significant levels of differentiation antigens in the plasma of breast cancer patients. The plasma of healthy control subjects had significantly lower antigen levels.

The procedure utilized highly diluted (1:100) human plasma samples which were dried at a pH of 2.1 on plastic microtiter plates. Monoclonal antibody (ascitic fluid diluted 1:1000) was then added to the microtiter plate. The amount of monoclonal reactive antigen was measured by a standard peroxidase enzyme system. Quantitation was achieved by constructing a standard dosage curve using a partially purified milk membrane preparation. Probably 1% of the membrane preparation was monoclonal-reactive differentiation antigen estimated by an eye scan of a Coomasse blue stained gel preparation. The position of the reactive antigen in the gel was identified by a Western blot.

METHODS

Plasma Samples: Blood samples collected in an EDTA or heparinized tube were utilized. Cell-free plasma was obtained by a two minute centrifugation in a Brinkman Model 5414 Table Top Cenrrifuge (15,000×G). Aliquots of plasma were stored at −70° C. Several studies were also done on blood samples received from the Corning Blood Collection Pool at Medford, Mass. These blood samples were collected in heparinized tubes and stored at −70° C.

Monoclonal Antibodies: Two monoclonal antibodies obtained from the Netherland Cancer Institute in Amsterdam were utilized. They are designated 115D8 and 67D11 and were obtained by standard hybridoma technology utilizing human antigens from purified human milkfat globule membranes. Spleen cells from immunized mice were fused to myeloma cells. Antibody screening assays were carried out with solid phase radioimmunoassays inVolving iodinated Protein A and standard ELISA assays.

ELISA Assay for the Detection of Epithelial Antigens in Human Plasma: Human plasma samples were diluted 1:100 in 20 mM citrate buffer at pH 2.1. Five (5) lambda of this diluted plasma was added to 45 lambda of citrate buffer in the well of a Costar microtiter plate. At this dilution of plasma, approximately 1700 nanograms of plasma protein were deposited in each microtiter well. The sample was dried overnight at 37° C. Plates were washed 3 times with PBS, pH 7.6, and 0.1% gelatin in PBS was added to fill the microtiter well (approx. 350 lambda). After 18 hours at 4° or 5 hours at 37° the plates were washed 10 times with PBS, pH 7.6, and 50 lambda of diluted monoclonal antibody (ascitic fluid diluted 1:1000 in 0.1% BSA, PBS, pH 7.6) was added. The plates were allowed to stand overnight at 4° C. and then washed 10× with PBS, and 50 lambda or sheep antimouse IgG conjugated with horseradish peroxidase was added for 60 minutes at room temperature. Cappel affinity-purified sheep antimouse IgG was used since it did not cross react with human IgG. The plates were washed 3 times with PBS, and 100 lambda of peroxidase substrate solution continuing equal parts of 0.03% Hydrogen peroxide and 0.2 mg/ml of ABTS [2′, 2′-azino-di(3-ethylbenzthiazoline-6-sulfonic acid)] were added. After 60 minutes the reaction was sropped with 50 lambda of 3 N sulfuric acid. The optical densities were read on a Dynatech Micro ELISA reader at a wavelength of 514 Å. From the standard curve, the nanogram/ml antigen level for each patient was calculated.

Standard curve: A standard dosage curve was established using partially purified antigen obtained from a human milk membrane preparation. The antigen level in the standard preparation was estimated to be 1% using an eye scan of an SDS gel. SDS-Western blot studies had shown the position of the reactive antigen in the gel and that it had a molecular weight greater than 200,000 daltons. The standard curve was established by adding known amounts of the antigen preparation to different microtiter wells. To this were added 1, 5, 10, 50, 100, 500, or 1000 nanograms of membrane preparation to different wells. The modified ELISA assay was performed. The OD value for each antigen level was recorded and a standard curve was plotted.

RESULTS

Studies were carried out utilizing five groups of human plasma samples: (1) 28 plasma samples from active breast cancer patients, (2) 32 normal subjects, (3) 13 plasma samples from patients with other types of cancer, (4) 10 plasma samples from women with benign breast disease (fibrocystic disease), and (5) 8 plasma samples from patients with altered physiology including 6 heparinized patients and 2 pregnant women.

Breast Cancer Patients: Plasma samples from 28 patients with acrive breast cancer were studied. These represented different stages of active disease, very early through wide metastases. By using a standard curve, the nanogram level of antigen/ml of human plasma was calculated. For women with breast cancer, the median plasma 115 antigen level was 500 ng/ml compared to a control median 115 antigen of 70 ng/ml. The median combined antigen level of breast cancer patients was 1100 ng compared to a median combined level of 90 ng/ml for control individuals. This difference between cancer patients and healthy controls, i.e., 1100 vs. 90, is highly significant.

The diagnostic discriminatory value of the ELISA assay is shown in Table 1. The best discrimination between cancer patients and healthy controls is achieved by using a combined antigen levels. It can be seen in Table 1 that using a combined antigen cutoff of 500 ng/ml, 26/28 (93%) of breast cancer patients are positive (antigens above this level), and no healthy controls (0/32) are positive at the 500 ng level. Using a single antigen level achieves less diagnostic discrimination. At the 300 ng antigen level it can be seen that 22/28 breast cancer patients are positive with 1/32 healthy controls positive, i.e., 92% breast cancer positive vs. 3% controls. Using a single antigen at higher cutoffs, i.e. 400 and 500 ng, the number and percent of positive cancer patients falls. With combined antigens at 500 ng/ml cutoff, 93% of breast cancer patients are positive and no healtny controls (0/32) are positive.

TABLE 1

| ELISA ASSAY DISCRIMINATION Patients/Controls: Number Positive at Different Antigen Levels | | | | |
|---|---|---|---|---|
| Antigen Level cutoff | Breast Cancer | | | Controls combined |
| | MC115 | MC67 | combined | |
| > 300 ng/ml | 23/28* | 22/28 | 24/28 | 1/32 |
| > 400 ng/ml | 17/24 | 18/24 | 24/24 | 1/32 |
| > 500 ng/ml | 12/24 | 12/24 | 26/28 | 0/32 |

*No. Positive/No. Studied

If the data on the ELISA assays is reviewed according to stage of disease, it can be seen that the combined antigen test is also highly discriminatory in patients with early breast cancer as well as in patients with more advanced disease. All (14/14 or 100%) early breast cancer patients were positive; 5/5 (100%) women with local recurrence and 8/9 (89%) of women with metastatic disease were also positive. No healthy controls, 0/32, were positive at the 500 ng level. The one negative patient in the metastatic category had been recently treated with X-ray to a localized bone deposit and also with heavy chemotherapy. She was listed clinically as "partially regressing". The results are shown in Table 2.

TABLE 2

| ELISA ASSAY RESULTS Different Stages of Breast Cancer Combined Antigen level above 500 ng/ml | | |
|---|---|---|
| | No. Positive | % Positive |
| Early breast cancer | 14/14 | 100 |
| Local recurrence | 5/5 | 100 |
| Metastatic | 8/9* | 89 |
| Controls | 0/32 | 0 |

*The one negative patient in this metastatic category had been treated with x-ray and heavy chemotherapy and was listed as "partially regressing".

Other types of cancers: Plasma samples from 13 patients with other types of cancer were studied. Table 3 shows the median plasma antigen levels of 1000 ng/ml (combined value) for colon patients; 400 ng/ml for ovarian, esophageal and lung cancer patients; and 500 ng/ml for leukemia patients. Melanoma patients were negative on the test (combined median levels less than 100). Of the total of 13 other cancer patients, 9 or 69% were positive on the combined antigen test.

TABLE 3

| OTHER CANCER PATIENT STUDIES Median Plasma Combined Antigen Levels | | | |
|---|---|---|---|
| Cancer Type | # Studied | # Positive* | Median Antigen Levels+ |
| Colon | 4 | 4 | 1000 |
| Melanoma | 2 | 0 | 100 |
| Ovary | 2 | 1 | 400 |
| Lung | 2 | 1 | 400 |
| Leukemia | 2 | 2 | 500 |
| Esophagus | 1 | 1 | 430 |
| Control | 33 | 0* | 100 |

*For cancer patients, based on a combined cutoff of 500 ng/ml.
For control combined cutoff of 500, no controls had combined levels above 500.
+Median antigen levels were based on combined 115D8 and 67D11 antigen levels.

Healthy control subjects: Plasma samples from 31 healthy control subjects were studied. The median plasma antigen levels for controls with the monoclonal 115D8 antigen was 70 ng/ml, the median 67D11 antigen level was 35 ng/ml, and the median combined antigen level was 90 ng. Table 1 (above) shows the number of control subjects positive at different antigen level cutoff values. It can be seen that in the combined antigen test at a cutoff value of 500 ng/ml, no control subjects (0/32) were positive.

Benign breast disease: Of the 10 women with benign breast disease studied, 4 had combined antigen levels above 500 ng. Thus, 4/10 or 40% were positive on the combined antigen test. The discrimination between benign and malignant breast disease by the monoclonal ELISA assay presents some problems. One helpful note is that most women with benign disease had elevated levels of 67D11 antigen, i.e., 300–350 ng, but had low 115D8 antigen levels, i.e., less than 100 ng.

Altered physiology: Two non-cancer categories of patients gave positive ELISA monoclonal assays: (1) Hospitalized patients receiving heparin and (2) pregnant women.

Heparin: Plasma samples from 6 hospitalized patients receiving heparin were studied. Table 4 shows the results of these studies. It can be seen that 3/6 (50%) of heparinized patients showed combined antigen levels above 500 ng/ml. Clinically this false positive category of patients would present few problems for the clinician in diagnostic situations.

TABLE 4
ELISA RESULTS
Other Conditions/Combined Antigen Levels > 500 ngm.

| | No. Positive/No. Studied | % pos. |
| --- | --- | --- |
| Benign breast disease | 4/10 | 40 |
| Heparinized patients | 3/6 | 50 |
| Pregnant women | 2/2 | 100 |

Pregnancy: Plasma samples from 2 pregnant women were studied on the ELISA assay, and both had combined antigen levels above 500 ng/ml. These results, are also shown in Table 4. Presumably these women are positive because of very high metabolic activity in the mammary gland tissue. Clinically false positive tests of pregnant women should not present diagnostic problems. very few breast cancers occur in women in the child bearing age, i.e., <30 years of age.

The invention now being fully described, it will apparent to one of ordinary skill in the art that many changes and modifications can be made thereto without departing from the spirit or scope of the invention as set forth herein.

What is claimed as new and desired to be secured by Letters Patent of the United States is:

1. A method for the detection of a human mammary epithelial differentiation antigen in a blood sample, which comprises:
    (a) conditioning said sample, by dissociating said antigen in said sample from binding proteins by adjusting the pH of said sample to within a range of from about 2 to 5;
    (b) drying said conditioned sample onto the surface of a test container to give a dried sample; and
    (c) adding a labeled antibody and detecting the label.
2. The method of claim 1, wherein said sample is conditioned by adjusting the pH to within a range of from about 2 to 4.
3. The method of claim 1, wherein said sample is conditioned by adjusting the pH to within a range of from about 2 to 3.
4. The method of claim 1, wherein said detecting comprises employing an immunological assay which utilizes a monoclonal antibody.
5. The method of claim 1, wherein said sample is plasma.
6. The method of claim 1, wherein said drying comprises heating at a temperature of no more than 55° C.
7. The method of claim 1, wherein said drying comprises heating at a temperature of no more than 42° C.
8. The method of claim 1, wherein said heating continues for no more than 36 hours at dryness.

* * * * *